United States Patent
Ashish et al.

(10) Patent No.: US 10,369,626 B2
(45) Date of Patent: Aug. 6, 2019

(54) PROCESS FOR THE PREPARATION OF BIO-ORGANIC COATED GOLD AND SILVER NANOPARTICLES USING BLUE LIGHT

(71) Applicant: Council of Scientific & Industrial Research, New Delhi (IN)

(72) Inventors: Ashish, Chandigarh (IN); Yogendra Singh Rathore, Chandigarh (IN); Nagesh Peddada, Chandigarh (IN); Kunzes Dolma, Chandigarh (IN); Renu Garg, Chandigarh (IN)

(73) Assignee: Council of Scientific & Industrail Research (IN)

( * ) Notice: Subject to any disclaimer, the term of this patent is extended or adjusted under 35 U.S.C. 154(b) by 0 days.

(21) Appl. No.: 15/561,625

(22) PCT Filed: Mar. 30, 2016

(86) PCT No.: PCT/IN2016/050097
§ 371 (c)(1),
(2) Date: Sep. 26, 2017

(87) PCT Pub. No.: WO2016/157220
PCT Pub. Date: Oct. 6, 2016

(65) Prior Publication Data
US 2018/0071818 A1 Mar. 15, 2018

(30) Foreign Application Priority Data
Mar. 30, 2015 (IN) .............................. 870/DEL/2015

(51) Int. Cl.
| | | |
|---|---|---|
| B22F 1/00 | (2006.01) | |
| B22F 9/24 | (2006.01) | |
| A61K 47/62 | (2017.01) | |
| A61K 47/69 | (2017.01) | |
| G01N 21/25 | (2006.01) | |
| G01N 21/78 | (2006.01) | |

(52) U.S. Cl.
CPC ............ *B22F 1/0062* (2013.01); *A61K 47/62* (2017.08); *A61K 47/6923* (2017.08); *B22F 1/0018* (2013.01); *B22F 1/0096* (2013.01); *B22F 9/24* (2013.01); *G01N 21/255* (2013.01); *G01N 21/78* (2013.01); *B22F 2301/255* (2013.01); *B22F 2999/00* (2013.01)

(58) Field of Classification Search
None
See application file for complete search history.

(56) References Cited

U.S. PATENT DOCUMENTS

2004/0191778 A1* 9/2004 Inaoka ................. G01N 33/538
435/6.12
2016/0271178 A1* 9/2016 Hauser .................... A61L 15/60

FOREIGN PATENT DOCUMENTS

WO 2016056028 4/2016

OTHER PUBLICATIONS

Tomita, Journal of Photochemistry and PhotobiologyB: Biology, 140, 2014 (Year: 2014).*
Sato Berru, Journal of Raman Spectroscopy, 40, 4, 2009 (Year: 2009).*
Abid, Chem Comm, 792-793, 2002 (Year: 2002).*
Yu, Angewandte Chemie International Edition, 53, 2014 with supporting information (Year: 2014).*
Joshi, Lanmuir, 22, 2006 (Year: 2006).*
Corresponding International Search Report for PCT/IN2016/050097 dated Aug. 9, 2016. WO.
Wang Jing et al: "Preparation of optically active Ag nanoparticles by UV light irradiation", Chinese Journal of Inorganic Chemistry/WU Ji Hua Xue Xue Bao, Chinese Electronic Periodical Services, CN, vol. 30, No. 8, Jan. 1, 2014, pp. 1889-1894, XP008180950, ISSN: 1001-4861. CN.
Morales Javier O et al: "Films loaded with insulin-coated nanoparticles (ICNP) as potential platforms for peptide buccal delivery" Colloids and Surfaces. B, Biointerfaces, Elsevier, Amsterdam, NL, vol. 122, Jun. 23, 2014, pp. 38-45, XP029063457, ISSN: 0927-7765, DOI: 10.1016/J.COLSURFB.2014.05.025. US.
Yanyan Yu et al: "Gelsolin bound [beta]-amyloid peptides (1-40/1-42): Electrochemical evaluation of levels of soluble peptide associated with Alzheimer's disease", Biosensors and Bioelectronics, vol. 68, Dec. 18, 2014, pp. 115-121, XP55292709, NL ISSN: 0956-5663, DOI: 10.1016/j.bios.2014.12.041. CN.
Sangeetha Krishnamurthy et al: "Lipid-coated polymeric nanoparticles for cancer drug delivery", Biomaterials Science, vol. 3, No. 7, Jan. 1, 2015, pp. 923-936, XP055291381, GB ISSN: 2047-4830, DOI: 10.1039/C4BM00427B the whole document. US.
Yazhuo Shang et al: "Synthesis of gold nanoparticles by reduction of HAuC14 under UV irradiation", Solid State Sciences, vol. 15, Jan. 1, 2013, pp. 17-23, XP55124303, ISSN: 1293-2558, DOI: 10.1016/j.solidstatesciences.2012.09.002 the whole document. CN.
Abou El-Nour K M M et al: "Synthesis and applications of silver nanoparticles", Arabian Journal of Chemistry, Saudi Chemical Society, SA, vol. 3, No. 3, Jul. 1, 2010, pp. 135-140, XP027079708, ISSN: 1878-5352, DOI: 10.1016/J.ARABJC.2010.04.008 [retrieved on Apr. 14, 2010] the whole document. SA.

(Continued)

*Primary Examiner* — Susan T Tran
*Assistant Examiner* — William Craigo
(74) *Attorney, Agent, or Firm* — The Belles Group, P.C.

(57) ABSTRACT

The present invention relates to a process which uses blue light to form bio-organic coated silver and gold nanoparticles for various applications. The present invention particularly relates to increasing the rates of reaction and widening the scope of tethering a range of biomolecules on the metal nanoparticles. The examples demonstrate that the biomolecules immobilized on the nanoparticles still retain many aspects of their structural elements which allow them to bind to their native binding partners and/or retain structural epitopes which allow them to be identified by antibodies specific to them, thus opening up scope of using such coated nanoparticles for functionalized and specific applications.

8 Claims, 4 Drawing Sheets
Specification includes a Sequence Listing.

(56) References Cited

OTHER PUBLICATIONS

Lorenzo Berti et al., "DAN-Templated Photoinduced Silver Deposition", (JACS) Journal of the American Chemical Society Communications, Jul. 21, 2005, J. AM. Chem. Soc. vol. 127, No. 32, 2005, National Research Center on nanoStructures and bioSystems at Surfaces S3, INFM-CNR, Via G. Campi 213/A, Modeno, Italy 41100.

Vinicius S Cardoso et al., "Collagen-based silver nanoparticles for biological applications: sysnthesis and characterization", Journal of Nanobiotechnology, 2014, http://www.jnanobiotechnology.com/content/12/1/36, pp. 1-9.

D. Matthew Eby et al., "Lysozyme Catalyzes the Formation of Antimicrobial Silver Nanoparticles", ACSNANO vol. 3, No. 4, pp. 984-994, www.acsnano.org, American Chemical Society 2009.

Emanuela Filippo et al., "Green synthesis of silver nanopartictes with sucrose and maltose: Morphological and structural characterization", Journal of Nom-Crystalline Solids, www.elsevier.com/locate/jnoncrysol, pp. 344-350, Department of Materials Science, Univeristy of Selento, Monteroni Street, Lecce, Italy 73100.

Krishnomurthy et al., "Lipid-coated polymeric nanoparticles for cancer drug delivery", The Royal Society of Chemistry Journal, Feb. 11, 2015, pp. 923-936.

Le Guevel, Xavier et al., "Synthesis and characterization of human transferrin-stabilized goid nanoclusters", 2011 Nanotechnology 22 275103, http://iopscience.iop.org/0957-4484/22/27/275103, pp. 1-7.

Mallik et al., Solution Structure Analysis of Cytoplasmic Domain of Podocyte Protein Neph1 Using Small/Wide Angle X-ray Scattering (SWAXS), The Journal of Biological Chemistry, col. 287, No. 12, pp. 9441-9453, Mar. 16, 2012, http://www.jbc.org/.

Tan et al., "Uncovering the Design Rules for Peptide Synthesis of Metal Nanoparticles", (JACAS) Journal of the American Chemical Society Articles, Mar. 31, 2010, vol. 132, No. 16, pp. 5677-5686, Cambridge, MA 02139.

Xie et al., "Protein-Directed Synthesis of Highly Fluorescent Gold Nanoclusters", (JACS) Journal of the American Chemical Society Communications, col. 131, No. 3, pp. 888-889, 2009, Institute of Bioengineering and Nanotechnology, Singapore 138669.

* cited by examiner (A)

SEQUENCE LISTING

```
<160> NUMBER OF SEQ ID NOS: 8

<210> SEQ ID NO 1
<211> LENGTH: 110
<212> TYPE: PRT
<213> ORGANISM: Artificial sequence
<220> FEATURE:
<223> OTHER INFORMATION: recombinant PDZ1-Zonula occludens ZOI protein

<400> SEQUENCE: 1

His His His His His His Ser Ser Gly Leu Val Pro Arg Gly Ser His
1               5                   10                  15

Met Ile Trp Glu Gln His Thr Val Thr Leu His Arg Ala Pro Gly Phe
            20                  25                  30

Gly Phe Gly Ile Ala Ile Ser Gly Gly Arg Asp Asn Pro His Phe Gln
        35                  40                  45

Ser Gly Glu Thr Ser Ile Val Ile Ser Asp Val Leu Lys Gly Gly Pro
    50                  55                  60

Ala Glu Gly Gln Leu Gln Glu Asn Asp Arg Val Ala Met Val Asn Gly
65                  70                  75                  80

Val Ser Met Asp Asn Val Glu His Ala Phe Ala Val Gln Gln Leu Arg
                85                  90                  95

Lys Ser Gly Lys Asn Ala Lys Ile Thr Ile Arg Arg Lys Lys
            100                 105                 110

<210> SEQ ID NO 2
<211> LENGTH: 20
<212> TYPE: PRT
<213> ORGANISM: Artificial sequence
<220> FEATURE:
<223> OTHER INFORMATION: Peptide-2 used for preparing silver and gold
      nanoparticles

<400> SEQUENCE: 2

Asp Ile Lys Val Glu Thr Val Asn Arg Glu Pro Leu Thr Met His Ser
1               5                   10                  15

Asp Arg Glu Asp
            20

<210> SEQ ID NO 3
<211> LENGTH: 20
<212> TYPE: PRT
<213> ORGANISM: Artificial sequence
<220> FEATURE:
<223> OTHER INFORMATION: Peptide-4 used for preparing silver and gold
      nanoparticles

<400> SEQUENCE: 3

Val Met Lys Ala Ile Tyr Ser Ser Phe Lys Asp Asp Val Asp Leu Lys
1               5                   10                  15

Gln Asp Leu His
            20
```

```
<210> SEQ ID NO 4
<211> LENGTH: 20
<212> TYPE: PRT
<213> ORGANISM: Artificial sequence
<220> FEATURE:
<223> OTHER INFORMATION: Peptide-9 used for preparing silver and gold
      nanoparticles

<400> SEQUENCE: 4

Ser His Ser Ser Gly Tyr Ala Gln Leu Asn Thr Tyr Ser Arg Ala Pro
1               5                   10                  15

Ala Ser Asp Tyr
            20

<210> SEQ ID NO 5
<211> LENGTH: 20
<212> TYPE: PRT
<213> ORGANISM: Artificial sequence
<220> FEATURE:
<223> OTHER INFORMATION: Peptide-13 used for preparing silver and gold
      nanoparticles

<400> SEQUENCE: 5

Pro Thr Tyr Arg Leu Gly Tyr Pro Gln Ala Pro Pro Ser Gly Leu Glu
1               5                   10                  15

Arg Thr Pro Tyr
            20

<210> SEQ ID NO 6
<211> LENGTH: 20
<212> TYPE: PRT
<213> ORGANISM: Artificial sequence
<220> FEATURE:
<223> OTHER INFORMATION: Peptide-14 used for preparing silver and gold
      nanoparticles

<400> SEQUENCE: 6

Glu Arg Thr Pro Tyr Glu Ala Tyr Asp Pro Ile Gly Lys Tyr Ala Thr
1               5                   10                  15

Ala Thr Arg Phe
            20

<210> SEQ ID NO 7
<211> LENGTH: 20
<212> TYPE: PRT
<213> ORGANISM: Artificial sequence
<220> FEATURE:
<223> OTHER INFORMATION: Peptide-15 used for preparing silver and gold
      nanoparticles

<400> SEQUENCE: 7

Thr Ala Thr Arg Phe Ser Tyr Thr Ser Gln His Ser Asp Tyr Gly Gln
1               5                   10                  15

Arg Phe Gln Gln
            20

<210> SEQ ID NO 8
<211> LENGTH: 76
<212> TYPE: DNA
<213> ORGANISM: Artificial sequence
<220> FEATURE:
<223> OTHER INFORMATION: Aptamer 10.10R of 76 bases
```

-continued

```
<400> SEQUENCE: 8
tcaagtggtc atgtactagt caagcacttt cgctgctcgc tggcgccgcg cccatcatat      60
gtccttctct tcccta                                                     76
```

PROCESS FOR THE PREPARATION OF BIO-ORGANIC COATED GOLD AND SILVER NANOPARTICLES USING BLUE LIGHT

CROSS-REFERENCE TO RELATED APPLICATIONS

This application is a National Stage of International Application No. PCT/IN2016/050097, filed Mar. 30, 2016, which claims priority to Indian Patent Application No. 870/DEL/2015, filed on Mar. 30, 2015. The disclosures of the above applications are incorporated herein by reference.

FIELD OF THE INVENTION

The present invention relates to a process for the preparation of bio-organic coated gold and silver nanoparticles using blue light. In particular, the present invention relates to increasing the rates of reaction and widening the scope of tethering a range of biomolecules on the metal nanoparticles. The biomolecules thus immobilized on the nanoparticles still retain many aspects of their structural elements which allow them to bind their native binding partners and/or retain structural epitopes which allow them to be identified by antibodies specific to them, thus opening up scope of using such coated nanoparticles for functionalized and specific applications in biomedical technology, electronics and communication, metal composition enrichment and recovery and biosensors.

BACKGROUND OF THE INVENTION

Despite various applications of metal nanoparticles in bio-imaging, drug or gene delivery, biosensor (Cardoso, Quelemes et al. 2014; Krishnamurthy, Vaiyapuri et al. 2015) etc., there remains a challenge in developing or formulating quick, non-toxic, eco-friendly, and stable nanoparticles by chemical or physical methods. Although the known methods are well optimized and capable of forming nanoparticles in different size ranges and in a short duration of time, the product displays toxic properties due to the chemicals involved in the formulations.

In the last two decades biological methods for the preparation of coated metal nanoparticles have been in practice which use whole microorganisms, microbial extracts, plant extracts and very recently few pure bio-origin materials such as proteins (BSA (Xie, Zheng et al. 2009), lysozyme (Eby, Schaeublin et al. 2009), transferrin (Le Guével, Daum et al. 2011), peptides (Tan, Lee et al. 2010), DNA (Berti, Alessandrini et al. 2005) and carbohydrates (Filippo, Serra et al. 2010) have also been used. However, their rate of formation is considerably slow and very high concentration of biomaterials is required to form the nanoparticles. Mostly the commonly available or so called model proteins are subjected to this kind of studies and exotic proteins have not been explored for the said purposes. Moreover, conditions optimized for one protein may or may not be applicable for other proteins. So, one pot synthesis of nanoparticles using proteins has not been successful till date. Though with increasing integration of technologies, role of biomaterial coated nanoparticles, particularly gold and silver nanoparticles (Au and Ag nanoparticles) is being increasingly considered, the following limitations have been observed holding back the translation thereof:

1) Synthesis of said nanoparticles requires at least two steps: a) chemical reduction based formation of uncoated base nanoparticles, b) coating of the nanoparticles with an adhering or tethering substance, c) binding of the proteinaceous molecules on the tethers. The latter may be anchored permanently or may release the protein molecules from its surface.
2) Co-formation may lead to encapsulation of the biomaterial which may not allow efficient use of the functional entity.
3) Direct functionalization or tethering requires extended times of reaction since bio-organic molecules do not possess the requisite reduction potential to simultaneously chelate and reduce. These extended timelines prove detrimental to the functional shape of the biomaterial in many instances.
4) Increment in temperature which has been applied to accelerate Ag and Au nanoparticles, does not work with bio-organic material which are used or intended to be used, as they denature with heat even in short durations of time.

Consequently, keeping in view the drawbacks of the hitherto reported prior art, it may be summarized that there is no prior art on the use of blue light to prepare bio-organic coated Ag and Au NPs, and there are no drawbacks envisioned today on use of blue light to prepare the coated/functionalized NPs, and related protocols. In light of the drawbacks in the prior art, there exists a dire need to provide a process that solves the problems associated with the formation/synthesis/biosynthesis of metal nanoparticles in a controlled manner using purified and characterized biomolecules such that the biomolecules coated on the nanoparticles still retain many aspects of their structural elements and functional aspects.

SUMMARY OF THE INVENTION

The main embodiment of the present invention provides a process for the preparation of bio-organic coated gold and silver nanoparticles using blue light, comprising the steps of:
(a) preparing a solution of $AgNO_3$ or $HAuCl_4$ in the range of 60-300 µM, optionally in a buffer having pH of 5 to 8 or in water having 0.1 to 300 mM NaCl;
(b) adding pure biomolecules to the solution prepared in step (a), wherein the molar ratio of biomolecule with $AgNO_3$ is 50:1 and with $HAuCl_4$ is 300:1;
(c) exposing the mixture of step (b) to blue light having a wattage in the range of 40 W to 200 W for 0.1 to 60 hours at a temperature of 30° C. to obtain the bio-organic coated gold and silver nanoparticles.

Another embodiment of the present invention provides a process as herein described wherein the buffer is selected from HEPES, tris, phosphate or trisodium citrate buffer.

Another embodiment of the present invention provides a process as herein described wherein the wavelength of blue light is in the range of 350 to 450 nm and has a wattage in the range of 40 to 200 W.

Another embodiment of the present invention provides a process as herein described wherein the biomolecules used are selected from the group consisting of peptides, antibodies, proteins, aptamers, oligonucleotides and small organic molecules of less than 700 Da.

Another embodiment of the present invention provides a process as herein described wherein the biomolecule is gelsolin.

Another embodiment of the present invention provides a process as herein described wherein the biomolecule is insulin.

Another embodiment of the present invention provides a process as herein described wherein the formation of bioorganic coated gold and silver nanoparticles is monitored by observing the color change of the reaction mixture or by measuring the absorbance of the solution at single wavelength of 420 nm to 550 nm for silver and gold nanoparticles respectively.

Another embodiment of the present invention provides a process as herein described wherein the color change of the reaction mixture from colorless to pale yellow to dark yellow indicates the formation of bio-organic coated silver nanoparticles.

Another embodiment of the present invention provides a process as herein described wherein the color change of the reaction mixture from colorless to light pink to purple indicates the formation of bio-organic coated gold nanoparticles.

LIST OF ABBREVIATIONS USED

| | |
|---|---|
| NPs | nanoparticles |
| Ag | Silver |
| Au | Gold |
| Ag NPs | Silver nanoparticles |
| Au NPs | Gold nanoparticles |
| TEM | Transmission Electron Microscopy |
| ELISA | Enzyme linked immune sorbent Assay |
| BSA | Bovine Serum Albumin |
| EGTA | Ethylene glycol tetra acetic acid |
| CaM | Calmodulin |
| t-PA | tissue plasminogen activator |
| PBS | Phosphate Buffer Saline |
| TMB | 3,3',5,5'-Tetramethylbenzidine |

DETAILED DESCRIPTION OF THE INVENTION

While the invention is susceptible to various modifications and/or alternative processes and/or compositions, specific embodiment thereof has been shown by way of example in the drawings and tables and will be described in detail below. It should be understood, however that it is not intended to limit the invention to the particular processes and/or compositions disclosed, but on the contrary, the invention is to cover all modifications, equivalents, and alternative falling within the spirit and the scope of the invention as defined by the appended claims.

The graphs, tables, figures and protocols have been represented where appropriate by conventional representations in the drawings, showing only those specific details that are pertinent to understanding the embodiments of the present invention so as not to obscure the disclosure with details that will be readily apparent to those of ordinary skill in the art having benefit of the description herein.

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention.

The terms "comprises", "comprising", or any other variations thereof, are intended to cover a non-exclusive inclusion, such that one or more processes or composition/s or systems or methods proceeded by "comprises . . . a" does not, without more constraints, preclude the existence of other processes, sub-processes, composition, sub-compositions, minor or major compositions or other elements or other structures or additional processes or compositions or additional elements or additional features or additional characteristics or additional attributes.

The present invention provides a process for the biosynthesis of bio-organic coated metal nanoparticles of silver and gold from their salt solutions by using different biomolecules including proteins, antibodies, DNA and small organic molecules by applying incident blue light.

In one aspect the present invention provides a process for preparing functionalized or coated metal nanoparticles particularly of silver and gold in a cost and time efficient manner. Thus the process of the present invention is a single step process which comprises mixing the two components (biomaterials and $AgNO_3$ or $HAuCl_4$ in a buffer comprising HEPES, Tris, phosphate orrisodium citrate at a pH in the range of 5 to 8 or in water having 0.1-300 mM NaCl followed by exposing the reaction mixture to blue light at a defined wattage and at a controlled temperature of 30° C.

Since the process of the present invention does not employ any harsh reaction conditions of temperature or pH, the properties of the biomolecules used therein remain unaltered. Thus, the process overcomes the problems encountered in making bio-organic coated metal nanoparticles particularly those with inert or native metals like silver and gold which can be directly used and have various applications e.g. as reporter/tracking electronics for communications, and/or biomedical applications, drug and/or targeting encapsulation, and/or formation or use in biosensors, and/or use in enrichment of precious metals from ores or solutions etc. In an embodiment of the present invention, the buffer is selected from HEPES, tris, phosphate or trisodium citrate buffer.

An aspect of the present invention provides bio-organic molecule or biomolecules disclosed herein range from small molecules, peptides, aptamers, proteins (including antibodies) to oligonucleotides.

Another aspect of the present invention exemplifies gelsolin which is having propensity to form silver nanoparticles, extensive permutations of the process conditions were explored to achieve biosynthesis of nanoparticles in a reproducible manner from other purified proteins, antibodies, DNA and small organic molecules. Likewise insulin is another exemplified biomolecule.

Another aspect of the present invention provides different conditions like protein to metal salt ratio (1:1000 to 1:40), buffers (varying from phosphate, Tris-HCl/glycine/tricine, sodium acetate, HEPES and the like), temperature (25-45° C.), and time of experimentation (30 minutes to 90 hours), pH of buffers (5-8), NaCl concentration in buffer (0.1-300 mM), and light intensities and wavelengths were varied to explore how different parameters affect rate of biosynthesis of nanoparticles. Follow-up transmission electron microscopy (TEM) experiments were done to confirm the size and shape of the metal nanoparticles. Later, experimental results demonstrated that the anchored or tethered or immobilized bio-organic molecules on the surface of nanoparticles can still retain their functional structure as they can bind their partner molecules and/or can be detected by their antibodies.

Thus an aspect of the present invention provides a method of forming metallic nanoparticles whereby reduction of a metal precursor to the metal is done in totality, comprising the steps of:
(a) mixing together the biomolecules with a metal precursor ($AgNO_3$ or $HAuCl_4$) that is to be reduced to form a mixture;
(b) Exposing the said mixture of $AgNO_3$ and bio molecules to 200 watt blue light at a controlled temperature of 30° C. for about 2 hours;
(c) Exposing the said mixture of $HAuCl_4$ and bio molecules to 200 watt blue light at controlled temperature of 30° C. for about 60 hours.

In another aspect the present invention provides a process wherein any chemical or biochemical modifications, chimeric version of bio-organic molecules, with tags and/or sequences in either C-terminus, N-terminus or N- and C-termini or in between protein sequence used for purification, tracking, characterization, partitioning, or folding of the resultant protein can be used.

In another aspect the present invention provides a method of biosynthesis of silver and gold nanoparticles coated with biomolecules wherein the reaction conditions comprise:
(a) variation in protein:metal ion ratio from 1:1000 to 1:40, temperature from 0-95° C., buffer composition, soluble salt in buffers with pH from 2-10.
(b) exposing white or blue light or green light or yellow light or red light or UV light (constant or variable) to initiate formation of nanoparticles.
(c) application of grated or collimated or specific wavelengths of light and/or laser (constant or variable) to initiate biosynthesis of nanoparticles by bio-organic molecules.
(d) exposing microwave or infrared (constant or variable) radiations to initiate or regulate biosynthesis of metal nanoparticles by bio-organic molecules and/or its any form.
(e) exposing magnetic field (constant or variable) to initiate or regulate biosynthesis of metal nanoparticles by bio-organic molecules and/or its any form.
(f) exposing electric field or voltage (AC and/or DC; constant or variable) to initiate or regulate biosynthesis of metal nanoparticles by bio-organic molecules and/or its any form.

In another aspect the present invention provides a process of biosynthesis of bio-organic coated metal nanoparticles useful for developing new assays, diagnostic, electronic/biosensor components, enrichment of metal from ores/solutions, recovery of native metals from natural or man-made compositions and pharmaceutical formulations.

In another aspect the present invention provides a process wherein the preferred wavelength of light is blue, however with extended exposure time, green and yellow light can also lead to the same results.

In another aspect the present invention provides that blue light having wavelength in the range of 350-450 nm and wattage in the range of 40 to 200 W are the dominating factors, whereas subsidiary factors like protein or bioorganic molecule or metal ion concentration, incubation temperature etc. are not so vital to achieve the final product or results.

In another aspect the present invention provides that the progress of the reactions can be monitored by observing the color change in the reaction mixture: colorless to pale yellow to darker yellow indicates the formation of bio-organic coated silver nanoparticles, and colorless to light pink to purple indicates the formation of bio-organic coated gold nanoparticles.

In another aspect the present invention provides an alternate means to monitor the progress of the reaction can be monitored by measuring the absorbance of the solution at a single wavelength of 420 nm and 550 nm for silver and gold nanoparticles, respectively. In another aspect the present invention another mode of monitoring the reaction can be by UV-Vis spectrophotometeric scan. Additionally, the shape and size of the nanoparticles can be measured from TEM images.

Advantages of the Invention

Biosynthesis of silver and gold nanoparticles using a known therapeutic protein and its variants will:
Lead to reproducible protocols.
Tinkering of protocols would lead to nanoparticles of specific shape and size.
The process involves Green Chemistry.
Post-synthesis, the particles may not require extensive processing prior to in vivo applications, if required.

Accordingly, the main embodiment of the present invention provides a process for the preparation of bio-organic coated gold and silver nanoparticles using blue light, comprising the steps of:
(a) preparing a solution of $AgNO_3$ or $HAuCl_4$ in the range of 60-300 μM, optionally in a buffer having pH of 5 to 8 or in water having 0.1 to 300 mM NaCl;
(b) adding pure biomolecules to the solution prepared in step (a), wherein the molar ratio of biomolecule with $AgNO_3$ is 50:1 and with $HAuCl_4$ is 300:1;
(c) exposing the mixture of step (b) to blue light having a wattage in the range of 40 W to 200 W for 0.1 to 60 hours at a temperature of 30° C. to obtain the bio-organic coated gold and silver nanoparticles.

Another embodiment of the present invention provides a process as herein described wherein the buffer is selected from HEPES, tris, phosphate or trisodium citrate buffer.

Another embodiment of the present invention provides a process as herein described wherein the wavelength of blue light is in the range of 350 to 450 nm and has a wattage in the range of 40 to 200 W.

Another embodiment of the present invention provides a process as herein described wherein the biomolecules used are selected from the group consisting of peptides, antibodies, proteins, aptamers, oligonucleotides and small organic molecules of less than 700 Da.

Another embodiment of the present invention provides a process as herein described wherein the biomolecule is gelsolin.

Another embodiment of the present invention provides a process as herein described wherein the biomolecule is insulin.

Another embodiment of the present invention provides a process as herein described wherein the formation of bio-organic coated gold and silver nanoparticles is monitored by observing the color change of the reaction mixture or by measuring the absorbance of the solution at single wavelength of 420 nm to 550 nm for silver and gold nanoparticles respectively.

Another embodiment of the present invention provides a process as herein described wherein the color change of the reaction mixture from colorless to pale yellow to dark yellow indicates the formation of bio-organic coated silver nanoparticles.

In another aspect the present invention provides that silver and gold nanoparticles can be made using different biomolecules and small organic compounds by the methods disclosed herein.

The process of preparation of the bio-organic coated metal nanoparticles comprises steps of:
(a) application of blue light (either source based, or applying some band pass filter on white light source, or using blue laser source) on a solution containing protein, DNA or small organic molecules.
(b) Addition of the biomolecule (protein, DNA or small organic molecules) in the $AgNO_3$ or $HAuCl_4$ solution made in buffer (HEPES, Tris, phosphate or trisodium citrate of pH 5-8) or water having NaCl in the range of 0.1-300 mM, wherein the biomolecule: metal salt ratio to form metal nanoparticles ranges from 1:1000 to 1:40.

In another aspect the present invention provides different biomolecules and organic compounds used in the process of the present invention.

In another aspect the present invention provides the conditions under which the process of the present invention is performed.

The following examples are given by way of illustration and therefore should not be construed to limit the scope of the invention in any manner.

EXAMPLES

Example 1

Blue Light Specifically Accelerates Formation of Ag and Au Nanoparticless in the Presence of Full-Length Gelsolin.

Figure 1:
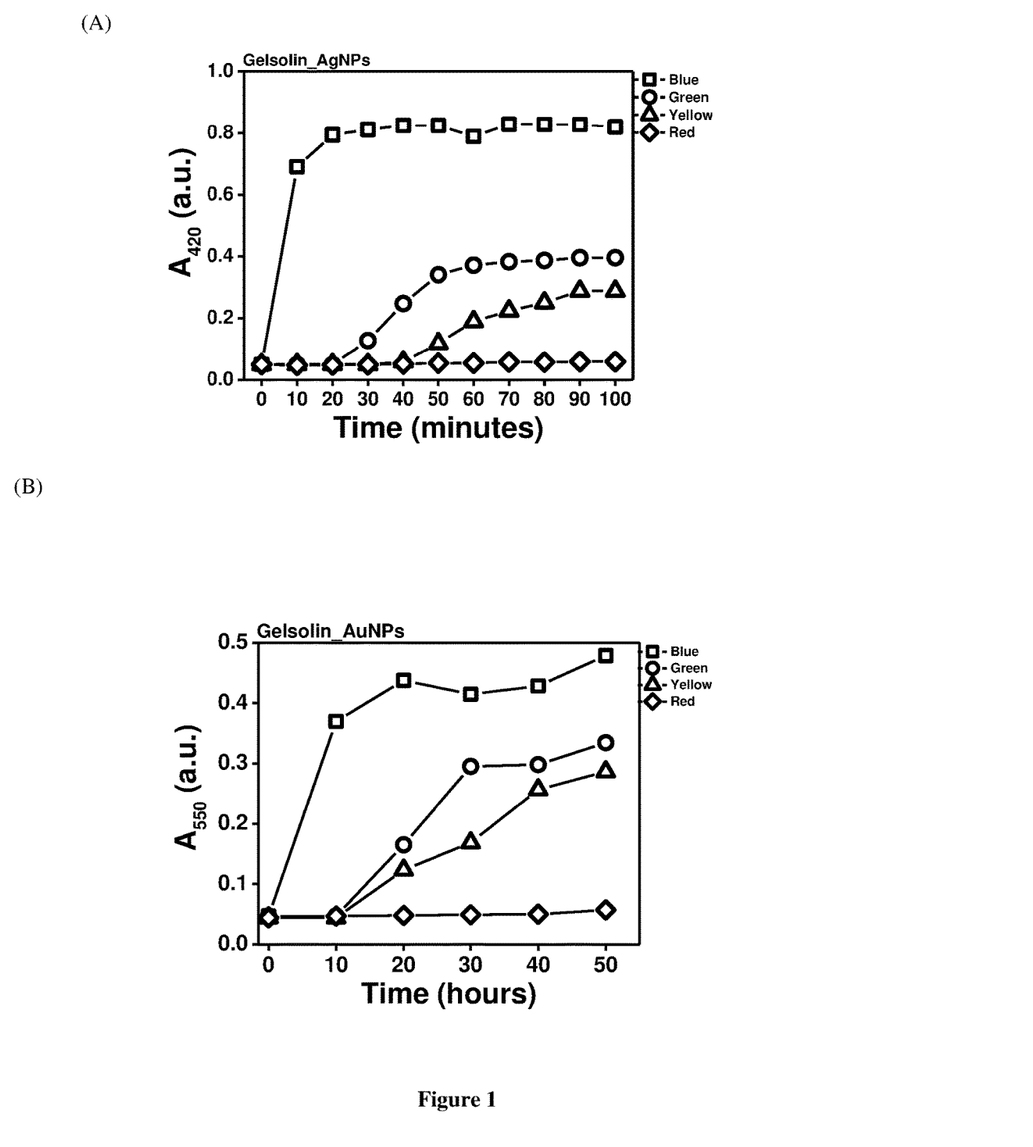
FIG. 1 illustrates that Blue light specifically accelerates formation of Ag and Au nanoparticles in the presence of human full-length gelsolin.

All experiments were performed with constant molar ratio of $AgNO_3$ or $HAuCl_4$ (Sigma) to gelsolin (Sigma) which was 50:1 for silver nanoparticles and 300:1 for Au nanoparticoles in solution, while $AgNO_3$ or $HAuCl_4$ concentration was in the range of 60-300 μM. Reaction mixture was prepared by adding 59.7 or 9.9 μl of gelsolin (stock concentration of 5 mg/ml) in each 1 ml of reaction volume of Tris buffer (50 mM Tris, 50 mM NaCl and 1 mM EGTA pH8) with 36 μl of $AgNO_3$ or $HAuCl_4$ of the 5 mM stock solution concentration to form Ag and Au nanoparticles, respectively. In this manner, the final molar ratio of Ag ions or Au ions to gelsolin was kept constant at 50:1 and 300:1, respectively. Color change from colorless to yellow color and characteristic absorbance peak in wavelength range of 400-500 or 500-600 nm are hallmarks of $AgNO_3$ or $HAuCl_4$ converting into Ag or Au nanoparticles, respectively. Source of the light supplied to the reaction mixture was 150 W-Tungsten-Halogen equipped Cold light (LB-150 Cold Light Illumination, COSLAB). Different colored broad range band pass filters (blue, green, yellow and red) were used for obtaining different wavelength light incident on the reaction mixture. Similarly, studies were conducted on nanoparticles formed in different conditions: Temperature (20-45° C.), pH (5-8), NaCl in buffers (0.1-300 mM), wherein only the rate of formation were found to be significantly different under varying conditions. FIGS. 1A and 1B represent Ag and Au nanoparticles formation using gelsolin in presence of different wavelengths of light such as blue, green, yellow, red and white light.

The results depicted in FIG. 1 illustrate the reactions of $AgNO_3$ to gelsolin ratio of 50:1 with $AgNO_3$ concentration of 180 μM and $HAuCl_4$ to gelsolin ratio of 300:1 with $HAuCl_4$ concentration of 180 μM. As evident from the said results, blue light gave the maximum yield of nanoparticles as compared to green and yellow light whereas, red light completely failed to trigger nanoparticle formation independent of exposure or reaction time. The two graphs clearly indicate that gelsolin based Ag and Au nanoparticle formation are specifically triggered by blue light having wavelength in the range of 360-450 nm. All the optical absorption measurements were carried out using UV-visible spectrophotometer (model CECIL CE7500 7000 series) equipped with quartz cuvette with path length 1 cm.

Example 2

Blue Light Based Formation of Ag Nanoparticles Using Wide Range of Biomaterials.

A wide range of biological and organic compounds can be used to form Ag and Au nanoparticles by applying blue light. Results are reported as a fold change which denotes absorbance of reaction mixture or other words is the amount of the nanoparticles formed, in presence of blue light divided by values in absence of any light. This value is indicative of the efficiency of formation of nanoparticles due to incident blue light. For all these experiments, a constant wattage of 200 W white light was used with Optical Band Pass filter in the range of 360-450 nm. To highlight the variance in the type of biomolecules which could provide these results or to uphold the general nature of this protocol being claimed, Isoelectric points (pI) and molecular masses of the proteins, antibodies, peptides, small molecules, and DNA are mentioned below each graph. The bio-organic molecule/compound's names is written over the bar showing the fold change.

Example 2[A]

Protein Based Silver and Gold Nanoparticles Formation

Reaction mixture of gelsolin (Sigma) based Ag or Au nanoparticles was prepared by adding 59.7 μl or 9.9 μl of gelsolin (5 mg/ml stock) in each 1 ml of reaction volume of tris buffer (50 mM Tris, 50 mM NaCl and 1 mM EGTA pH8) with 36 μl of $AgNO_3$ or $HAuCl_4$ of 5 mM stock solution to form Ag or Au nanoparticles, respectively. The final molar ratio of silver ions and gold ions to gelsolin was kept constant at 50:1 and 300:1. Similarly reaction mixture of bovine serum albumin (BSA) (Sigma), hen egg white lysozyme (Sigma), bovine insulin (Sigma), recombinant human tissue plasminogen activator (t-PA) (Actilyse, Boehringer Ingelheim GmbH & Co. KG, Germany), calmodulin (CaM, Sigma), recombinant PDZ1-Zonula occludens ZOI (SEQ ID No. 1), Streptavidin (Thermo scientific), and bovine RNaseA (Sigma) based Ag or Au nanoparticles was prepared by mixing 49.8 µl or 8.3 µl of BSA (5 mg/ml), 10.4 µl or 1.7 µl of lysozyme (5 mg/ml), 20.5 µl or 3.4 µl of bovine insulin (1 mg/ml, prepared in water at pH 2), 75.5 µl or 12.6 µl of t-PA (3 mg/ml, prepared in water supplied commercially), 15.1 µl or 2.5 µl of CaM (4 mg/ml), 8.7 µl or 1.5 µl of PDZ1-ZO1 (5 mg/ml), 16.4 µl or 2.7 µl of Streptavidin (5 mg/ml), and 16.4 µl or 2.7 µl of bovine RNaseA (3 mg/ml), in each 1 ml of reaction volume of phosphate buffer saline (PBS, pH 7.4) with 36 µl of $AgNO_3$ and $HAuCl_4$ of 5 mM stock solution to form Ag and Au nanoparticles, respectively. The final molar ratio of silver ions and gold ions to the proteins listed above was kept constant at 50:1 (Ag nanoparticles) and 300:1 (Au nanoparticles), respectively.

Example 2[B]

Peptides Based Silver and Gold Nanoparticles Formation

Similarly in case of peptides stock solution of 3 mg/ml was prepared in tris buffer (25 mM Tris and 40 mM NaCl pH 8). Freshly prepare 2 mM $AgNO_3$ or $HAuCl_4$ in element free water (Q-pod, 18S2M water resistivity). Enlisted peptides in Table 1 include Pep-2 (SEQ ID NO: 2), Pep-4 (SEQ ID NO: 3), Pep-9 (SEQ ID NO: 4), Pep-13 (SEQ ID NO: 5), Pep-14 (SEQ ID NO: 6) and Pep-15 (SEQ ID NO: 7) which are random 20 amino acid stretches synthesized using solid phase F-moc click chemistry. Pep-2 (572.4 µl or 35.8 µl), Pep-4 (564.7 µl or 35.8 µl), Pep-9 (391.4 µl or 24.5 µl), Pep-13 (543.3 µl or 34 µl), Pep-14 (564 µl or 35.2 µl) and Pep-15 (578.1 µl or 36.1 µl), volumes of peptide (3 mg/ml) were mixed in tris buffer of 1 ml each consisting of 90 µl of 2 mM stock solution of $AgNO_3$ or $HAuCl_4$, respectively. The final molar ratio of silver ions and gold ions to each peptide was kept constant at 1:4 and 4:1, respectively.

TABLE 1

TABLE OF SEQUENCES USED IN THE INVENTION

| SEQ ID No. | NAME OF THE SEQUENCE | SEQUENCE |
|---|---|---|
| SEQ ID NO. 1 | PDZ1-ZO1 | HHHHHHSSGLVPRGSHMIWE QHTVTLHRAPGFGFGIAISG GRDNPHFQSGETSIVISDVL KGGPAEGQLQENDRVAMVNG VSMDNVEHAFAVQQLRKSGK NAKITIRRKK |
| SEQ ID NO. 2 | Pep-2 | DIKVETVNREPLTMHSDRED |
| SEQ ID NO. 3 | Pep-4 | VMKAIYSSFKDDVDLKQDLH |
| SEQ ID NO. 4 | Pep-9 | SHSSGYAQLNTYSRAPASDY |
| SEQ ID NO. 5 | Pep-13 | PTYRLGYPQAPPSGLERTPY |
| SEQ ID NO. 6 | Pep-14 | ERTPYEAYDPIGKYATATRF |
| SEQ ID NO. 7 | Pep-15 | TATRFSYTSQHSDYGQRFQQ |

TABLE 1-continued

TABLE OF SEQUENCES USED IN THE INVENTION

| SEQ ID No. | NAME OF THE SEQUENCE | SEQUENCE |
|---|---|---|
| SEQ ID NO. 8 | Aptamer 10.10R of 76 bases | tcaagtggtcatgtactagt caagcactttcgctgctcgc tggcgccgcgcccatcatat gtccttctcttcccta |

Example 2[C]

Small Organic Molecules Based Silver and Gold Nanoparticles Formation

In case of small molecules based Ag or Au nanoparticles formation, 180 µl or 7.2 µl of each stock solution of 0.5M (Glycine, Sucrose and Urea) were added to water (pH7) having 36 µl of 5 mM $AgNO_3$ or $HAuCl_4$, respectively. The final molar ratio of silver ions and gold ions to each small molecule was kept constant at 2:1 (Ag nanoparticles) and 50:1 (Au nanoparticles), respectively.

Example 2[D]

Oligonucleotides Based Silver and Gold Nanoparticles Formation

Similarly in case of oligonucleotides such as pGEMT-vector (Promega) and aptamer 10.10R of 76 bases (SEQ ID NO: 8) were used. Reaction mixture was prepared by mixing 113.7 µl or 2.28 µl of pGEMT-vector (25.7 ng/µl) in each 0.5 ml of reaction volume (water, pH 7) with 9 µl of $AgNO_3$ or $HAuCl_4$ of 10 mM stock solution to form Ag or Au nanoparticles, respectively. The final molar ratio of silver ions and gold ions to pGEMT-vector was kept constant at 1:1 and 50:1, respectively. While in case of aptamer 10.10R, reaction mixture was prepared by adding 18 µl or 0.9 µl of aptamer (4.86 µg/µl) in each 0.2 ml of reaction volume of buffer (25 mM tris pH 8, 150 mM NaCl, 5 mM $MgCl_2$, 10 mM KCl, 0.01% tween and 2 mM $CaCl_2$) with 7.2 µl of $AgNO_3$ or $HAuCl_4$ of 5 mM stock solution to form Ag or Au nanoparticles, respectively. The final molar ratio of silver ions and gold ions to aptamer was kept constant at 10:1 and 200:1, respectively.

Example 2[E]

Antibodies Based Silver and Gold Nanoparticles Formation

In case of Anti-His antibody (Thermo scientific) reaction mixture was prepared by adding 13.5 µl or 3.4 µl of Anti-His antibody (1 mg/ml) in each 0.25 ml of reaction volume of PBS (pH 7.4) with 4.5 µl of $AgNO_3$ or $HAuCl_4$ of 10 mM stock solution to form Ag or Au nanoparticles, respectively. The final molar ratio of silver ions or gold ions to Anti-His antibody was kept constant at 500:1 or 2000:1, respectively. While in case of Goat anti-rabbit-HRP antibody (Thermo scientific) reaction mixture was prepared by adding 8.7 µl or 3.5 µl of Goat anti-rabbit-HRP antibody (0.4 mg/ml) in each 0.2 ml of reaction volume of PBS (pH 7.4) with 3.6 µl of $AgNO_3$ or $HAuCl_4$ of 10 mM stock solution to form Ag or Au nanoparticles, respectively. The final molar ratio of silver ions or gold ions to Anti-His antibody was kept constant at 2000:1 or 5000:1, respectively.

Figure 2:
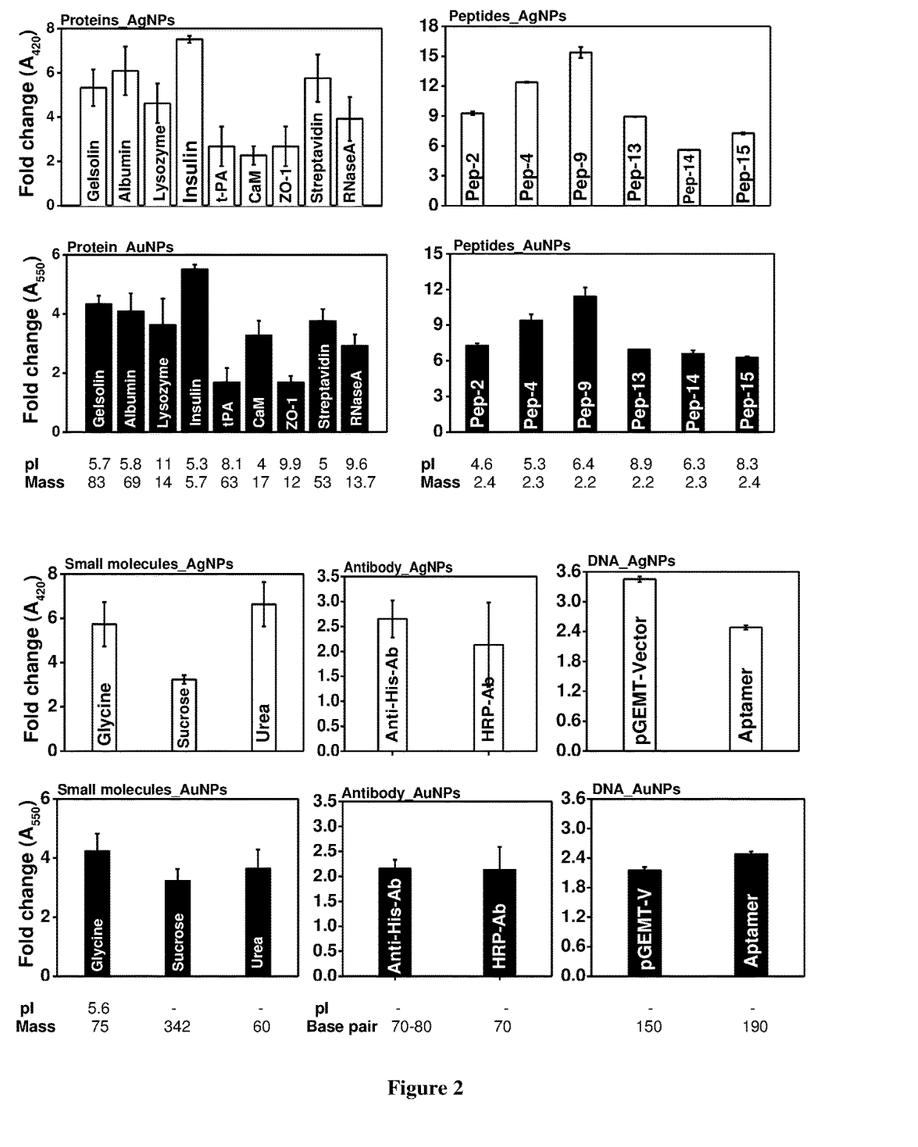
FIG. 2 illustrates the Blue light based formation of Ag nanoparticles using wide range of Biomaterials.

In all the above experiments 2[A] to 2[E] duplicates of each sample were subjected to two conditions of presence of 200 W blue light and in absence of light, in an incubator with controlled temperature of 30° C. Control samples were also kept which includes reaction mixture without the biomolecules. Further each sample of Ag and Au nanoparticles fabricated using different biomolecules were tracked using UV-visible spectrophotometer reading of the colloidal solutions at 420 nm and 550 nm after exposure time of 60 minutes and 60 hours, wherein both reactions were carried out in presence and absence of light. FIG. 2 illustrates the results obtained in each case which is the fold change in the reading of Ag and Au nanoparticles at its maximum wavelength in presence and absence of light.

Example 3

Formation of Gelsolin and Insulin Mediated Ag or Au Nanoparticles Using Blue Light Depend on the Power (Wattage) of the Source Used.

Different watt bulbs (25 W, 40 W, 60 W, 100 W and 200 W) were used as source of light (Philips bulb). Reaction mixture of gelsolin (Sigma) based Ag nanoparticles or Au nanoparticles was prepared by adding 59.7 µl or 9.9 µl of gelsolin (5 mg/ml) in each 1 ml of reaction volume of tris buffer (50 mM Tris, 50 mM NaCl and 1 mM EGTA pH8) with 36 µl of $AgNO_3$ or $HAuCl_4$ of 5 mM stock solution to form Ag or Au nanoparticles, respectively. Reaction mixture of bovine insulin (Sigma) based Ag or Au nanoparticles was prepared by adding 20.5 µl or 3.4 µl of bovine insulin (1 mg/ml, prepared in water at pH 2) in each 1 ml of reaction volume of PBS (pH 7.4) with 36 µl of $AgNO_3$ or $HAuCl_4$ of 5 mM stock solution to form Ag or Au nanoparticles, respectively. The final molar ratio of silver ions or gold ions to the gelsolin or Insulin was kept constant at 50:1 (Ag nanoparticles) or 300:1 (Au nanoparticles), respectively. Further the reaction was exposed to light of different wattage and incubated at 30° C.

Example 3[A]

Change of Color from Colorless to Yellow and Pinkish Indicated Formation of Ag Nanoparticles and Au Nanoparticles Respectively.

Figure 3:
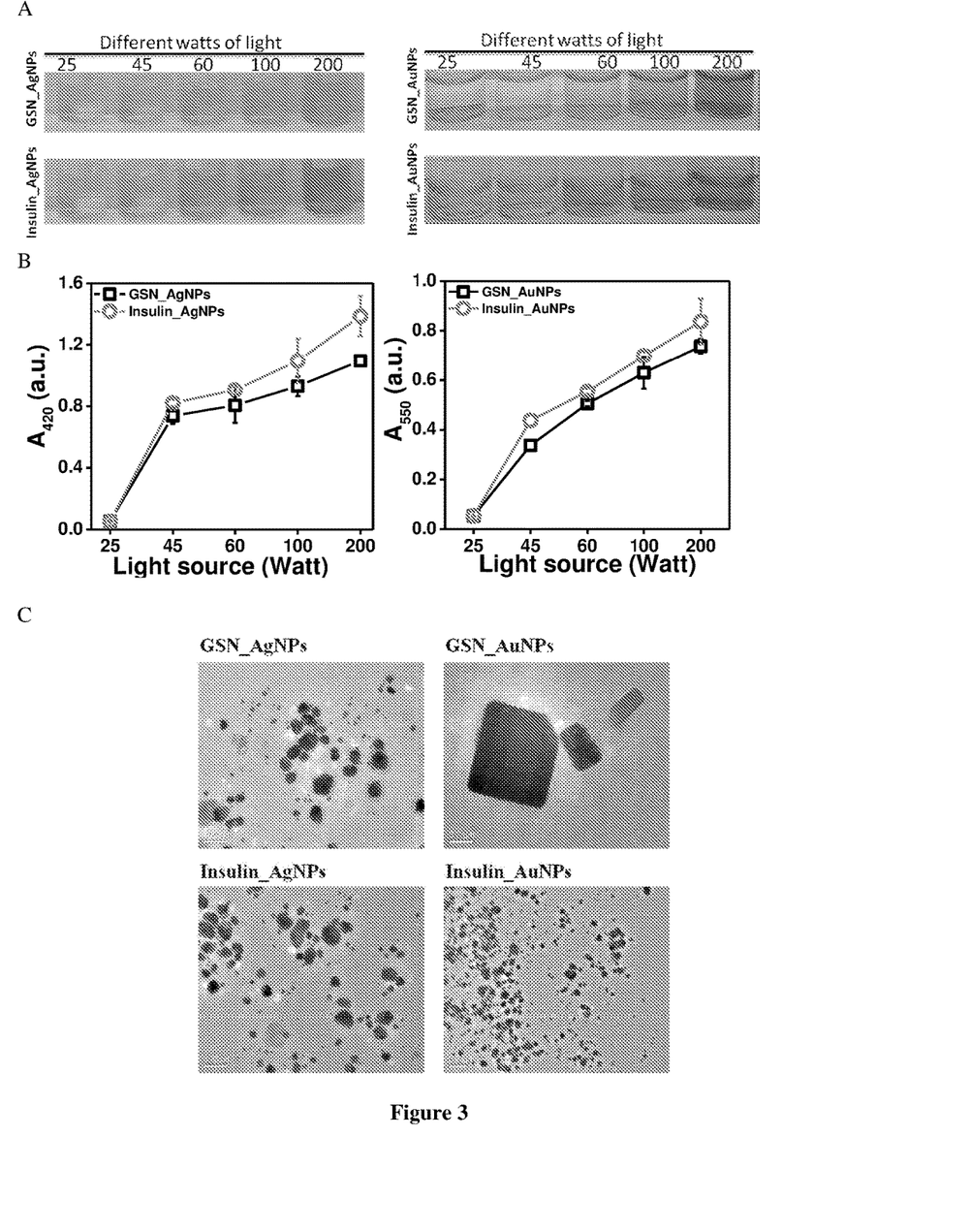
FIG. 3 illustrates that formation of gelsolin and insulin mediated Ag or Au nanoparticles using blue light are dependent on the power (wattage) of the source used. (a) Change of color from colorless to yellow and pinkish indicated formation of Ag nanoparticles and Au nanoparticles respectively. (b) Increase in absorbance value at 420 or 550 nm supported an increase in amount of Ag or Au nanoparticle formation respectively, as a function of source watts keeping same time frame of experiment (2 to 60 hours). (c) TEM image of the gelsolin and insulin based Ag or Au nanoparticles at 200 W blue light after 2 or 60 hours of exposure time respectively.

First indication of nanoparticles formation in each case was tracked using the change in color of reaction mixture from colorless to yellowish and pinkish color in case of Ag and Au nanoparticles respectively. The yield of nanoparticles was tracked using optical absorption measurements carried out using UV-visible spectrophotometer. Apart from blue light, intensity of light also contributes to efficiency of proteins to get excited and donate electrons to the metal ions thus forming metal nanoparticles. Results showed in FIG. 3A indicate that in the presence of 25 W light power there is no change in color indicating that this power of light is not enough to induce both Ag and Au nanoparticles. However, in all the other wattage of light (40 W, 60 W, 100 W and 200 W), there is clear conversion of color and increase in its intensity with increase in power of light.

Example 3[B]

Increase in Absorbance Value at 420 or 550 nm Supported an Increase in Amount of Ag or Au Nanoparticle Formation as a Function of Source Watts Keeping Same Time Frame of Experiment (2 or 60 Hours).

Gelsolin and insulin based Ag or Au nanoparticles formed at different wattage of light were further confirmed by using UV-visible spectrophotometer reading of the colloidal solutions at 420 nm/550 nm after exposure time of 2 or 60 hours in presence of 200 W blue light. The change in absorbance value with increase in wattage of light correlates very well with the change in color of reaction mixture mentioned above. FIG. 3B (left (Ag nanoparticles) and right (Au nanoparticles)) also clearly indicate that at 25 W, the absorbance value at 420 nm or 550 nm is comparable to control samples suggesting there is no nanoparticle formation in this condition. However, at all the other wattage of light from 40-200 W, there is significant change in absorbance value at the characteristic wavelength indicating formation of Ag or Au nanoparticles in case of both gelsolin and insulin.

Example 3[C]

TEM Image of the Gelsolin and Insulin Based Ag or Au Nanoparticles at 200 W Blue Light after 2 to 60 Hours of Exposure Time.

Further confirmation of the gelsolin and insulin based Ag or Au nanoparticles formed in presence of light was provided by transmission electron microscopy (TEM, model JOEL 1200Ex II). Here we considered only the gelsolin and insulin based Ag or Au nanoparticles formed at 200 W blue light. In this carbon coated copper grids were soaked with 10 µl of the gelsolin and insulin coated Ag nanoparticles and Au nanoparticles for 10 minutes, which were air dried and further mounted on the sample holder of TEM. After multiple TEM images were obtained, most uniformly sized particles were chosen as in sample image displayed with the scale (in nm). FIG. 3C illustrates that the samples of gelsolin based Ag nanoparticles displayed non-uniform shaped and 20-60 nm size particles, however in case of Au nanoparticles the particles were bigger and uniform shaped (square/rectangle) of 100-400 nm size. Whereas in case of insulin based Ag and Au nanoparticles both were non uniform and within size range of 40-80 nm (FIG. 3C).

Example 4

ELISA of Nanoparticles Formed Using Three Different Proteins, Aptamer and Antibody to Confirm their Capping on the Nanoparticles Surface.

Example 4[A]

Indirect ELISA to Confirm Presence of Protein on the Surface of Ag and Au Nanoparticles Proteins including gelsolin (Sigma), insulin (Sigma) and PDZ1-ZO1 (Mallik, Arif et al. 2012) (SEQ ID NO. 1) were considered according to the availability of antibodies to check their retention of binding against the specific antibody after the completion of process of nanoparticles formation. Reaction mixture of gelsolin based Ag or Au nanoparticles was prepared by adding 59.7 µl or 9.9 µl of gelsolin (5 mg/ml) in each 1 ml of reaction volume of tris buffer (50 mM Tris, 50 mM NaCl and 1 mM EGTA pH8) with 36 µl of $AgNO_3$ or $HAuCl_4$ of 5 mM stock solution to form Ag or Au nanoparticles, respectively. Further the reaction mixture was incubated at 30° C. and 200 W blue light for 2 to 60 hours for Ag or Au nanoparticles, respectively. Control samples of only gelsolin were prepared by adding 59.7 µl (Ag nanoparticles control) or 9.9 µl (Au nanoparticles control) of gelsolin (5 mg/ml) in each 1 ml of reaction volume of tris buffer (50 mM Tris, 50 mM NaCl and 1 mM EGTA pH8) making final concentration of gelsolin 3.6 µM or 0.6 µM, respectively. Similarly, in case of bovine insulin (Sigma) based Ag or Au nanoparticles the reaction mixture was prepared by adding 20.5 µl or 3.4 µl of bovine insulin (1 mg/ml, prepared in water at pH2) in each 1 ml of reaction volume of PBS (pH 7.4) with 36 µl of AgNO$_3$ or HAuCl$_4$ of 5 mM stock solution to form Ag or Au nanoparticles making final concentration of bovine insulin 3.6 or 0.6 µM, respectively. Control samples of only bovine insulin were prepared by adding 20.5 µl or 3.4 µl of bovine insulin (1 mg/ml, prepared in water at pH 2) in each 1 ml of reaction volume of PBS (pH 7.4) making final concentration of bovine insulin 3.6 µM or 0.6 µM, respectively. Likewise reaction mixture of PDZ1-ZO1 (Mallik, Arif et al. 2012) (SEQ ID NO. 1) based Ag or Au nanoparticles was prepared by adding 8.7 µl or 1.5 µl of PDZ1-ZO1 (SEQ ID NO. 1) (5 mg/ml) in each 1 ml of reaction volume PBS (pH 7.4) with 36 µl of AgNO$_3$ or HAuCl$_4$ of 5 mM stock solution to form Ag or Au nanoparticles making final concentration of PDZ1-ZO1 (SEQ ID NO. 1) 3.6 µM or 0.6 µM, respectively. Control samples of only PDZ1-ZO1 (SEQ ID NO. 1) were prepared by adding 8.7 µl or 1.5 µl of PDZ1-ZO1 (SEQ ID NO. 1) (5 mg/ml) in each 1 ml of reaction volume of PBS (pH 7.4) making final concentration of PDZ1-ZO1 (SEQ ID NO. 1) 3.6 µM or 0.6 µM, respectively. Further the reaction mixtures in case of all three proteins were incubated at 30° C. and 200 W blue light for 2 to 60 hours for Ag or Au nanoparticles, respectively to form bio-organic coated nanoparticles. Control samples for only nanoparticles were prepared using citrate based method. To form Ag or Au nanoparticles, 20 µl or 1 µl of trisodium citrate (1M) was added to 5 ml of water having 5 µl or 1 µl of AgNO$_3$ or HAuCl$_4$ heated to 80° for 5 minutes and further boiled the solution for 15 minutes to form citrate based Ag or Au nanoparticles.

Samples 1 includes 1) Gelsolin Ag nanoparticles (3.6 µM gelsolin), 2) Gelsolin_Au nanoparticles (0.6 µM gelsolin), and control samples having only gelsolin 3) 3.6 µM and 4) 0.6µ M.

Sample 2 includes 1) Insulin Ag nanoparticles (3.6 µM Insulin), 2) Insulin Au nanoparticles (0.6 µM Insulin), and control samples having Insulin 3) 3.6 µM and 4) 0.6 µM. Sample 3 includes 1) PDZ1-ZO1_Ag nanoparticles (3.6µ M PDZ1-ZO1), 2) PDZ1-ZO1 Au nanoparticles (0.6 µM PDZ1-ZO1), and control samples having PDZ1-ZO1 3) 3.6 µM and 4) 0.6 µM.

Similarly the control samples of citrate based Ag and Au nanoparticles were characterized using UV-visible spectrophotometer reading resulting from absorbance at 425 nm and 533 nm respectively. In order to normalize the concentration of citrate nanoparticles to protein nanoparticles, the citrate nanoparticles were diluted according to the absorbance value of protein nanoparticles. Samples coated were 50 µl, 25 µl, 12.5 µl and 6.25 µl (Protein Agnanoparticles), 100 µl, 50 µl, 25 µl and 12.5 µl (Protein Au nanoparticles) and their respective control samples both positive (only proteins) and negative (only citrate nanoparticles) and volume make up was performed using coating buffer (100 mM NaHCO$_3$ pH 9.2). Maxisorp 96-well plate with the samples was further incubated at 4° C. for overnight. To saturate excess binding sites on the coated material blocking was done by 3% bovine serum albumin (BSA) in PBS and kept at room temperature for 2 hours. The wells are then washed three times with PBST and 100 µl of 1:3000 diluted rabbit polyclonal anti-gelsolin or Polyclonal rabbit anti-insulin IgG or 6x-His epitope Tag mouse monoclonal antibody was added to respective wells with gelsolin or insulin or His-tagged PDZ1-ZO-1 (SEQ ID NO. 1), respectively and incubated for another 2 hours. The wells were washed as above and incubated with 1:8000 diluted chicken anti-rabbit IgG-HRP for 1 hour at room temperature followed by addition of the substrate (TMB) solution (Pierce) and once the color developed, stopped the reaction with 2M H$_2$SO$_4$. The absorbance was measured with a multiskan ELISA reader at 450 nm.

Figure 4:
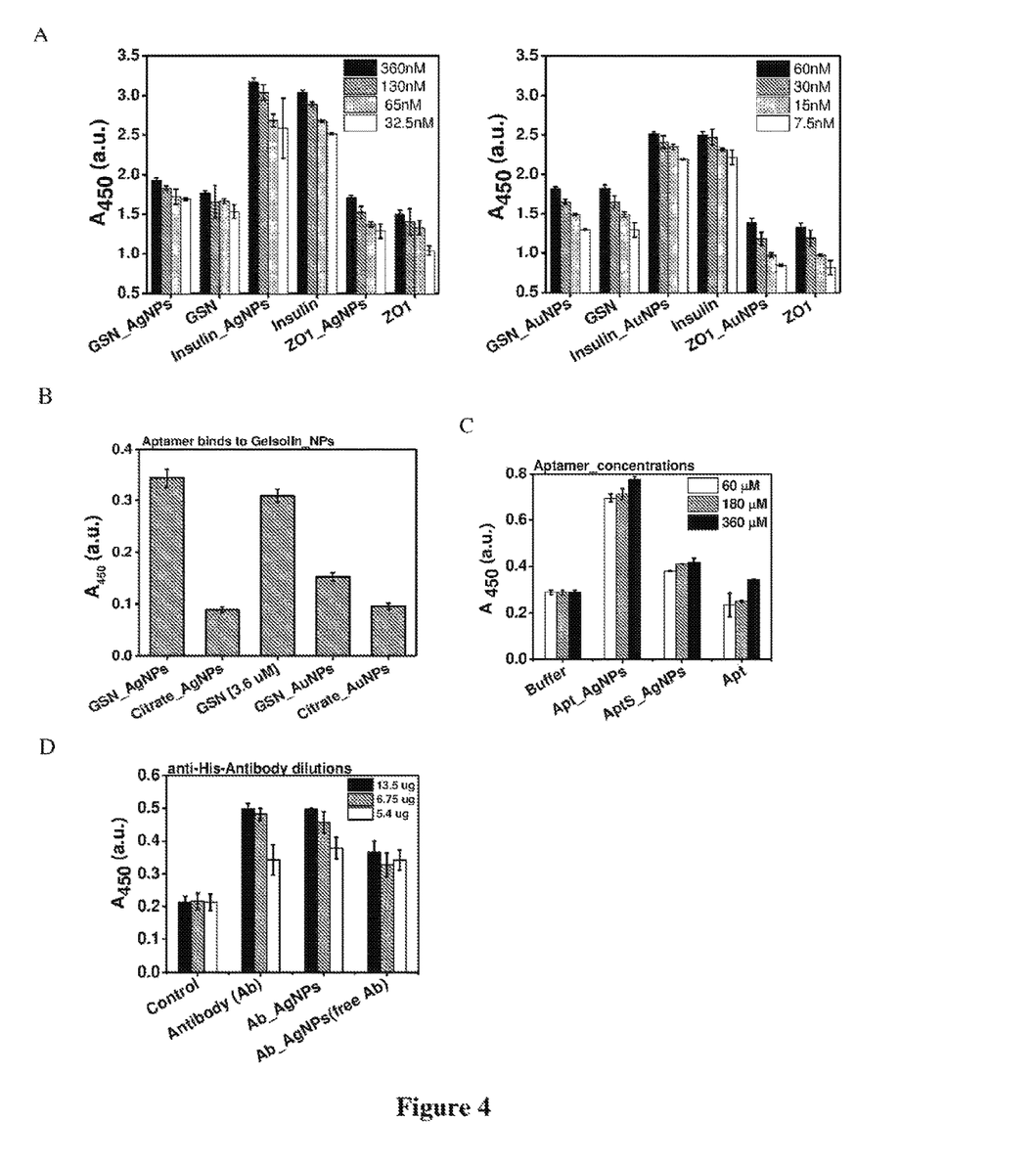
FIG. 4 illustrates the ELISA of nanoparticles formed using three different biomolecules viz., proteins, aptamers and antibody to confirm their capping on the nanoparticles surface. (a) Indirect ELISA to confirm presence of protein on the surface of Ag and Au nanoparticles. (b) Indirect ELISA based estimation of functionality of gelsolin coated on Ag using its aptamer binding property. (c) Indirect ELISA based estimation of functionality of aptamer coated on Ag nanoparticles using its gelsolin binding property. (d) Sandwich-ELISA of anti-His-antibody and anti-His-antibody Ag nanoparticles to confirm functionality of anti-His-antibody coated on Ag nanoparticles.

In case of all the three proteins (FIG. 4A, left (Ag nanoparticles) and right (Au nanoparticles)), the trend of decrease in absorbance value at 450 nm with decrease in concentration of protein control of each sample correlates very well with the dilution of the Ag and Au nanoparticles formed by the individual proteins. The data represented here shows the value of absorbance after subtracting the background absorbance obtained in case of citrate based nanoparticles. The result clearly indicates that functional protein is present on the surface of nanoparticles that were also involved in nanoparticles formation.

Example 4[B]

Indirect ELISA Based Estimation of Functionality of Gelsolin Coated on Ag or Au Nanoparticles Using its Aptamer Binding Property Reaction mixture of gelsolin based Ag or Au nanoparticles was prepared by adding 59.7 µl or 9.9 µl of gelsolin (5 mg/ml) in each 1 ml of reaction volume of tris buffer (50 mM Tris, 50 mM NaCl and 1 mM EGTA pH8) with 36 µl of AgNO$_3$ or HAuCl$_4$ of 5 mM stock solution to form Ag or Au nanoparticles respectively. Further the reaction mixture was incubated at 30° C. and 200 W blue light for 2 to 60 hours for Ag or Au nanoparticles, respectively. Control samples of only gelsolin were prepared by adding 59.7 µl (Ag nanoparticles control) or 9.9 µl (Au nanoparticles control) of gelsolin (5 mg/ml) in each 1 ml of reaction volume of tris buffer (50 mM Tris, 50 mM NaCl and 1 mM EGTA pH8) making final concentration of gelsolin 3.6 or 0.6 µM respectively. Control samples for nanoparticles were prepared using citrate based method. To form Ag or Au nanoparticles, 20 µl or 1 µl of trisodium citrate (1M) was added to 5 ml of water having 5 µl or 1 µl of AgNO$_3$ or HAuCl$_4$ heated to 80° C. for 5 minutes and further boiled the solution for 15 minutes to form citrate based Ag or Au nanoparticles. Gelsolin Ag or Au nanoparticles were characterized using UV-visible spectrophotometer reading of the colloidal solutions at 420 nm or 550 nm after exposure time of 2 or 60 hours in presence of 200 W blue light, respectively. Similarly, the control samples of citrate based Ag or Au nanoparticles were characterized using UV-visible spectrophotometer reading obtained for absorbance at 425 nm and 533 nm, respectively. Samples include Gelsolin Ag nanoparticles (3.6 µM gelsolin), gelsolin only (3.6 µM), Gelsolin_Au nanoparticles (0.6 µM gelsolin), and citrate based Ag or Au nanoparticles (absorbance value normalized with gelsolin Ag or Au nanoparticles, to 1.2 and 0.65 by dilution). After coating the 100 µl sample in triplicates in Maxisorp 96-well plate it was incubated at 4° C. for overnight. 10 µl of Aptamer 10.10R (SEQ ID No. 8) (18 µM) was added to each well with 90 µl coating buffer after three times washing with PBS and incubated for another 2 hours at room temperature. Further, followed by washing step with PBST, HRP-Streptavidin (Thermo Fisher) was coated and again incubated for another 1 hour at room temperature. After the completion of incubation time, again washing was performed and then 100 µl substrate (TMB) solution (Pierce), was added and once color was developed, stopped the reaction with 2M H$_2$SO$_4$. The absorbance was measured with a multiskan ELISA reader at 450 nm. FIG. 4B clearly shows the comparable absorbance value at 450 nm in case of gelsolin only and gelsolin_Ag nanoparticles at same concentration of 3.6 µM. Absorbance value in case of gelsolin_Au nanoparticles also correlates well with concentration of protein (0.6 µM). In addition, control samples of citrate based Ag or Au nanoparticles showed no binding to aptamer. The result clearly indicates gelsolin coated on nanoparticles preserves full retention of binding to aptamer.

Example 4[C]

Indirect ELISA Based Estimation of Functionality of Aptamer Coated on Ag Nanoparticles Using its Gelsolin Binding Property In case of aptamer based Ag nanoparticles formation, reaction mixture was prepared by adding 18 µl of Aptamer 10.10R (SEQ ID No. 8) (4.86 µg/µl or 18 pmoles/µl) in each 0.2 ml of reaction volume of buffer (25 mM tris pH 8, 150 mM NaCl, 5 mM $MgCl_2$, 10 mM KCl, 0.01% tween and 2 mM $CaCl_2$) with 7.2 µl of $AgNO_3$ of 5 mM stock solution to form Ag nanoparticles. The final molar ratio of silver ions to aptamer 10.10R was kept constant at 10:1. Treated the ELISA plate with 1 µg/well streptavidin (1 mg/ml) and incubated the plate overnight at 4° C. For aptamer based Ag nanoparticles coating streptavidin was not used. The wells were blocked with 3% bovine serum albumin (BSA) in PBS and kept at room temperature for 2 hours to saturate excess binding sites. The wells were then washed three times with PBST and further added with 5, 10 and 20 µl of aptamer only and aptamer Ag nanoparticles (18 pmoles/µl), making aptamer working concentration of 90, 180 and 360 µM. All the coatings were performed in duplicates for two conditions one with and one without gelsolin in next step. After completion of incubation time of 2 hours at 200 rpm and room temperature, washing was performed three times with 1×PBST. Further, in one set of duplicate wells added gelsolin (2 µg/well) and in other set added only buffer (50 mM Tris, 50 mM NaCl and 1 mM EGTA pH8) and again incubated for 2 hours at 200 rpm and room temperature. The wells were then washed three times with PBST and 100 µl of 1:3000 diluted rabbit polyclonal anti-gelsolin antibody was added and incubated for 2 hours. The wells were washed as mentioned above and further incubated with 1:8000 diluted chicken anti-rabbit IgG-HRP (Thermo Fisher) for 1 hour at room temperature followed by addition of the substrate (TMB) solution (Pierce). Once the color developed, the reaction was stopped with 2M $H_2SO_4$. The absorbance was measured with a multiskan ELISA reader at 450 nm.

It was observed that the coated aptamer or aptamer_Ag nanoparticles were captured by gelsolin which was further detected using anti-gelsolin antibody using an indirect ELISA based method (FIG. 4C). Control samples were coating buffer (with or without gelsolin), aptamer_Ag nanoparticles or aptamer Supernatant Ag nanoparticles (with or without gelsolin) and aptamer only (positive control, with/without gelsolin). Further, the readings obtained in case of "without gelsolin samples" were than subtracted from the "with gelsolin samples" for every sample. The results clearly depict 3 times more binding capability of Aptamer 10.10R (SEQ ID No. 8) coated on Ag nanoparticles than only aptamer towards gelsolin.

Example 4[D]

Sandwich-ELISA of Anti-his-Antibody and Anti-his-Antibody Ag Nanoparticles to Confirm Functionality of Anti-his-Antibody Coated on Ag Nanoparticles Anti-His antibody (Thermo scientific) reaction mixture was prepared by adding 13.5 µl of Anti-His antibody (1 mg/ml) in each 0.25 ml of reaction volume of PBS (pH 7.4) with 4.5 µl of $AgNO_3$ of 10 mM stock solution to form Ag nanoparticles. The final molar ratio of silver ions to Anti-His antibody was kept constant at 500:1. Only Anti-His antibody was prepared by adding 13.5 µl of Anti-His antibody (1 mg/ml) in each 0.25 ml of reaction volume of PBS (pH 7.4). In the entire case 0.054 mg/ml antibody which was 18.5 times diluted was used. Before using, the antibody based Ag nanoparticles were washed three times with PBS and used both the pellet with nanoparticles only and also the supernatant as the residual nanoparticles were visible in the form of color. Finally, the coating antibody concentration in both antibody Ag nanoparticles and only antibody for three dilutions of 1:400, 1:800 and 1:1000 were screened and incubated for overnight at 4° C. Each sample was kept in duplicates in two sets; one with and another without gelsolin in next step after blocking with 3% bovine serum albumin (BSA) for 2 hours at room temperature to saturate excess binding sites. The wells were then washed three times with PBST and one set was added with gelsolin (2 µg/well) and in other set only added buffer (50 mM Tris, 50 mM NaCl and 1 mM EGTA pH8) and again incubated for 2 hours at 200 rpm and room temperature. The wells were then washed three times with PBST and 100 µl of 1:3000 diluted rabbit polyclonal anti gelsolin antibody was added and incubated for 2 hours. The wells were washed as mentioned above and further incubated with 1:8000 diluted chicken anti-rabbit IgG-HRP (Thermo scientific) for 1 hour at room temperature followed by addition of the substrate (TMB) solution (Pierce). Once the color developed, the reaction was stopped with 2M $H_2SO_4$. The absorbance was measured with a multiskan ELISA reader at 450 nm.

It was observed that gelsolin was captured by the coated anti-His-antibody and anti-His-antibody based Ag nanoparticles which were further detected using anti-gelsolin antibody. Control samples were coating buffer (with or without gelsolin), anti-His-antibody Ag nanoparticles or anti-His-antibody Ag nanoparticles supernatant (with or without gelsolin) and anti-His-antibody only (positive control, with or without gelsolin). Further, the reading obtained in case of "without gelsolin samples" were than subtracted from the "with gelsolin samples" for every sample. The result (FIG. 4D) clearly depicts the higher binding capability of anti-His-antibody coated on Ag nanoparticles than only anti-His-antibody towards gelsolin as the supernatant of anti-His-antibody Ag nanoparticles having unbound or very small Ag nanoparticles showed signs of binding with gelsolin.

REFERENCES

Berti, L., A. Alessandrini, et al. (2005). "DNA-templated photoinduced silver deposition." Journal of the American Chemical Society 127(32): 11216-11217.

Cardoso, V. S., P. V. Quelemes, et al. (2014). "Collagen-based silver nanoparticles for biological applications: synthesis and characterization." Journal of nanobiotechnology 12(1): 36.

Eby, D. M., N. M. Schaeublin, et al. (2009). "Lysozyme catalyzes the formation of antimicrobial silver nanoparticles." ACS nano 3(4): 984-994.

Filippo, E., A. Serra, et al. (2010). "Green synthesis of silver nanoparticles with sucrose and maltose: Morphological and structural characterization." Journal of Non-Crystalline Solids 356(6): 344-350.

Krishnamurthy, S., R. Vaiyapuri, et al. (2015). "Lipid-coated polymeric nanoparticles for cancer drug delivery." Biomaterials science 3(7): 923-936.

Le Guével, X., N. Daum, et al. (2011). "Synthesis and characterization of human transferrin-stabilized gold nanoclusters." Nanotechnology 22(27): 275103.

Mallik, L., E. Arif, et al. (2012). "Solution structure analysis of cytoplasmic domain of podocyte protein Nephl using small/wide angle x-ray scattering (SWAXS)." Journal of Biological Chemistry 287(12): 9441-9453.

Tan, Y. N., J. Y. Lee, et al. (2010). "Uncovering the design rules for peptide synthesis of metal nanoparticles." Journal of the American Chemical Society 132(16): 5677-5686.

Xie, J., Y. Zheng, et al. (2009). "Protein-directed synthesis of highly fluorescent gold nanoclusters." Journal of the American Chemical Society 131(3): 888-889.

Ashish et al, Aptamers for purifying and quantifying gelsolin and its variants. Indian Appl No. 2852DEL2014, Jul. 10, 2014 (PATENT FILED)

We claim:

1. A process for the preparation of bio-organic coated gold nanoparticle or bio-organic coated silver nanoparticles using blue light, comprising the steps of:
    (a) preparing a solution of AgNO$_3$ or HAuCl$_4$ in the range of 60-300 μM, optionally in a buffer having pH of 5 to 8 or in water having 0.1 to 300 mM NaCl;
    (b) adding pure biomolecules to the solution prepared in step (a), wherein the molar ratio of AgNO$_3$ to biomolecule is 50:1 or the molar ratio of HAuCl$_4$ to biomolecule is 300:1, wherein the biomolecules are selected from the group consisting of peptides, antibodies, proteins, aptamers and oligonucleotides;
    (c) exposing the mixture of step (b) to blue light having a wattage in the range of 40 W to 200 W for 0.1 to 60 hours at a temperature of 30° C. to obtain the bio-organic coated gold nanoparticle or bio-organic coated silver nanoparticles.

2. The process as claimed in claim 1, wherein the buffer is selected from HEPES, tris, phosphate or trisodium citrate buffer.

3. The process as claimed in claim 1, wherein the wavelength of blue light is in the range of 350 nm to 450 nm.

4. The process as claimed in claim 1, wherein the biomolecule is gelsolin.

5. The process as claimed in claim 1, wherein the biomolecule is insulin.

6. The process as claimed in claim 1, wherein the formation of bio-organic coated gold nanoparticles or bio-organic coated silver nanoparticles is monitored by observing color change of the mixture or by measuring the absorbance of the mixture at single wavelength of 420 nm for bio-organic coated silver nanoparticles or at single wavelength of 550 nm for bio-organic coated gold nanoparticles.

7. The process as claimed in claim 6, wherein the color change of the mixture from colorless to pale yellow to dark yellow indicates the formation of bio-organic coated silver nanoparticles.

8. The process as claimed in claim 6, wherein the color change of the reaction mixture from colorless to light pink to purple indicates the formation of bio-organic coated gold nanoparticles.

* * * * *